United States Patent [19]

Kantrowitz et al.

[11] 4,051,840

[45] Oct. 4, 1977

[54] DYNAMIC AORTIC PATCH

[75] Inventors: Adrian Kantrowitz, Pontiac; Paul S. Freed, Oak Park, both of Mich.

[73] Assignee: Sinai Hospital of Detroit, Detroit, Mich.

[21] Appl. No.: 645,735

[22] Filed: Jan. 5, 1976

[51] Int. Cl.² .......................... A61M 1/03; A61F 1/24
[52] U.S. Cl. ........................................ 128/1 D; 3/1.7
[58] Field of Search ................... 128/1 D, 214 R, 344; 3/1.7

[56] References Cited

U.S. PATENT DOCUMENTS 3,585,983  6/1971  Kantrowitz et al. ................. 128/1 D
3,766,567  10/1973  Kahn et al. ...................... 128/1 D X

OTHER PUBLICATIONS

Kantrowitz et al. — Trans. Amer. Soc. Artif. Inter. Orgs., 1972, pp. 159–167.

Primary Examiner—Dalton L. Truluck
Attorney, Agent, or Firm—Cullen, Settle, Sloman & Cantor

[57] ABSTRACT

An improved dynamic aortic patch is surgically implanted in the thoracic aorta and is systematically inflated and deflated to generate pressure waves in the bloodstream. The pressure waves assist the heart by augmenting the circulation of the blood through the body. The patch includes a flexible inflatable bladder and an independent envelope. The envelope has a reinforced surface for limiting and directing inflation of the bladder inwardly toward the lumen of the aorta.

4 Claims, 6 Drawing Figures

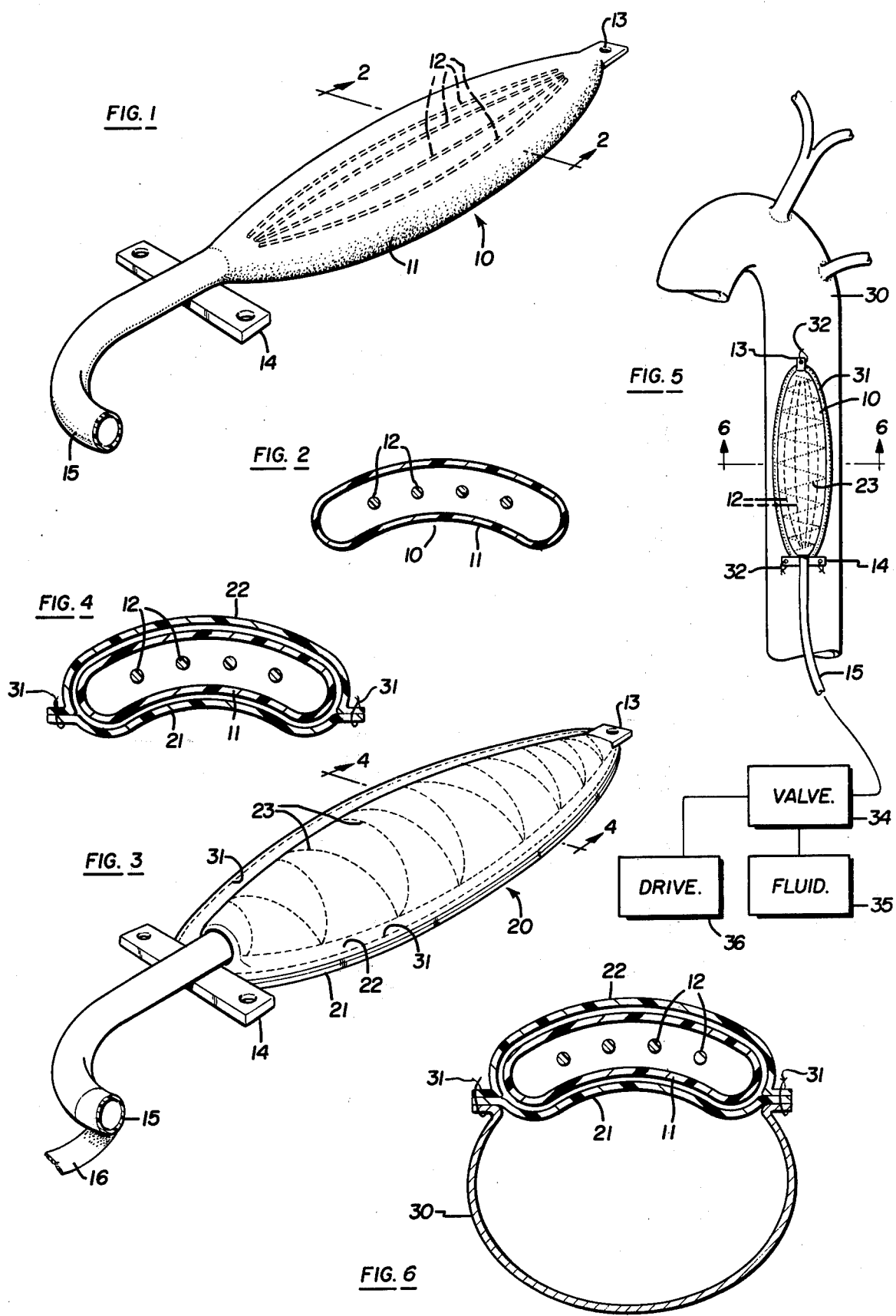

DYNAMIC AORTIC PATCH

BACKGROUND OF THE INVENTION

The invention was made in the course of work under grants from the Department of Health, Education and Welfare.

The invention relates generally to heart assist devices and, more particularly, to an auxiliary ventricle which augments the circulation of the blood through the body. A dynamic aortic patch is a mechanical auxiliary ventricle which is surgically implanted in the descending thoracic aorta and which provides a movable vessel wall at the location of the implantation. The patch is systematically inflated and deflated by the application of fluidic pressure to move the wall of the patch and thus generate pressure waves in the bloodstream. These pressure waves support the heart by augmenting the circulation of blood thus increasing coronary flow.

A dynamic aortic patch is a permanently implanted circulatory assist device intended for use in supporting the circulation of patients whose cardiac action is chronically inadequate and cannot be restored by established medical or surgical techniques. It is designed to support the heart by augmenting the circulation of blood to the coronary vessels and peripheral vasculature.

The original dynamic aortic patch included a flexible bladder to which was cemented a Dacron covering sheet which was non-thrombogenic. The use of the initial dynamic aortic patch was published in "Transactions of the American Society of Artificial Internal Organs," Volume XVIII, Page 159 (1972), and in "Transplant Proceedings," Volume III, p. 1459 (1971).

The dynamic aortic patch as previously published included a flexible hollow tube connected to the bladder. The bladder was systematically inflated and deflated by the introduction of fluid pressure, such as compressed gas, through the tube and into the bladder. During the implantation of the bladder extracorporeal bypass was necessary.

Various problems were noted with the original dynamic aortic patch. At first, since the bladder and cover were cemented together prior to implantation, there was always the inherent danger of damaging the bladder by puncturing it during suturing. This, of course, significantly increased the time necessary to implant the apparatus and hence the time that the patient was on a heart-lung machine.

Second, if it was necessary to later replace the bladder component because of normal wear, the entire apparatus had to be removed and a new patch sutured in place. This, again, required extracorporeal bypass.

Hence, the present invention overcomes these problems by providing an improved dynamic aortic patch having none of these shortcomings.

SUMMARY OF THE INVENTION

The present invention provides an improved dynamic aortic patch including separable bladder and envelope components. The envelope is sutured in place during extracorporeal bypass. Extracorporeal bypass is terminated and the bladder is inserted into the envelope. Hence, there can be no damage by puncturing the bladder during the implantation of the envelope.

By use of distinct, discrete bladder and envelope components, when it is necessary to replace the bladder component at a later time, it is not necessary to utilize extracorporeal bypass. A portion of the envelope is opened and the complete bladder is removed and a new bladder is inserted.

The bladder includes longitudinal reinforcing filaments which prevent the bladder from closing upon itself and entrapping gas therein.

BRIEF DESCRIPTION OF THE DRAWINGS

The foregoing advantages of the present invention, together with other advantages which may be attained by its use, will become more apparent upon reading the following detailed description taken in conjunction with the drawings. In the drawings, wherein like reference numerals identify corresponding components:

FIG. 1 is a perspective illustration of the inflatable bladder of the present invention;

FIG. 2 is a cross sectional view of the bladder as seen in the plane of arrows 2—2 of FIG. 1;

FIG. 3 is a perspective illustration of the dynamic aortic patch with the bladder inserted within the envelope;

FIG. 4 is a cross sectional view of the dynamic aortic patch as seen in the plane of arrows 4—4 of FIG. 3;

FIG. 5 is a schematic representation of the implantation of the dynamic aortic patch and the operation of the dynamic aortic patch; and FIG. 6 is a cross section of the implanted patch as seen in the plane of arrows 6—6 of FIG. 5.

DETAILED DESCRIPTION OF THE INVENTION

By way of background, it is, of course, understood there are certain primary requirements for a surgically implanted dynamic aortic patch. The bladder itself must be air tight and sufficiently flexible to expand and deflate at the required speeds and pressures. The envelope or covering material presents a surface to the blood and, of course, this surface must be non-thrombogenic. When the envelope is implanted, the implantation contact surface between the envelope and the incised vessel wall must be air tight to prevent leakage of blood into the thoracic cavity. These requirements are well understood by those skilled in the art.

Referring more particularly to the drawings, there is illustrated first the inflatable bladder 10 of the present invention which, in a preferred embodiment, is cylindrically shaped polyurethane film 11 which is 0.18 mm thick. The flexible bladder measures 15.0 cm along its longitudinal axis and 3.0 cm in width and is capable of inflation to a volume of 35 cc. Enclosed interiorly of the bladder 10 are elongated polyurethane filaments 12 which are disposed parallel to the longitudinal axis of the bladder 10. These filaments prevent the inner walls of the bladder from closing together in response to the surrounding blood pressure during deflation of the bladder and thus gas will not be trapped interiorly of the bladder during bladder deflation.

Each end of the bladder includes a tab 13, 14 for suturing the bladder in place with tab 13 being a longitudinal protrusion at the distal end of the bladder and tab 14 being a transverse member at the front end. At the front end of the bladder there is a hollow flexible tube 15 which, in a preferred embodiment, is made of polyurethane reinforced with stainless steel wire. The tube 15 is wrapped with Dacron velour 16 and defines a fluid flow path to the interior of the bladder.

The envelope 20 into which the bladder is removably inserted is fabricated of a Dacron velour. The surface 21 which becomes the blood interface, i.e., the surface which faces the interior or lumen of the descending thoracic aorta is backed with a conductive polyurethane. This promotes the growth of a pseudointima and also provides a low potential for thromboembolism.

The other surface 22 of the envelope, i.e., the surface which faces the thoracic cavity, is also Dacron velour and is cross stitched as at 23. This prevents the surface 22 of the envelope from stretching and thus limits and directs the inflation of the bladder inwardly toward the lumen of the thoracic aorta.

To implant the aortic patch, the descending thoracic aorta 30 is incised along its longitudinal axis preferably starting just below the origin of the subclavian artery. The envelope 20 is sutured to the walls of the incision as at 31 with the surface 21 of the envelope joined to the intima of the vessel in an air tight relationship. The bladder is inserted in the envelope and the tabs 13, 14 sutured in place as at 32.

The supply tube 15 is connected to a valve 34 which is coupled to a source of fluid 35 preferably compressed gas.

In order to activate the patch, a driving unit 36 is utilized. The driving unit controls the application of the compressed gas to inflate and deflate the bladder. Specifically, electrodes are sutured into the myocardium at the time of surgery and the "R" wave of the electrocardiograph triggers the drive unit which provides gas at a pressure of 2—3 psi to inflate the bladder to a volume of 35 cc.

As illustrated in FIGS. 3 and 5, the cross stitching 23 limits the ability of the bladder to inflate toward the thoracic cavity and substantially limits and directs the inflation of the bladder inwardly of the thoracic aorta 30. Furthermore, the filaments 12 prevent collapse of the patch and entrapment of gas therein, in response to pressure of the blood against surface 21 of the envelope.

In operation, the use of the "R" wave from the electrocardiograph activates the valve which operates to contract the patch out of phase with the physiologic left ventricle, decreasing systolic heart pressure, and thus reducing the work of the left ventricle. Aortic pressure is increased during diastole, again out of phase, providing normal peripheral perfusion and increasing mean arterial flow. This is called counter pulsation and is well known.

When the dynamic aortic patch is inactive, there is no interference with the physiologic flow of blood through the arterial tree and peripheral circulation.

If the bladder of the present invention should require replacement, it is only necessary to open the upper facing 22 of the envelope 20, remove the bladder 10 and insert a new bladder. To accomplish this, since the lower surface 21 of the envelope remains intimately in contact with the walls of the thoracic aorta, extracorporeal bypass is not necessary. Similarly, since the entire lower surface 21 of the envelope 20 is sutured to the vessel before the bladder is inserted, there is minimal risk of puncturing the bladder. This permits not only quicker, easier, safer initial implantation of the apparatus, but also permits faster replacement of the bladder since only the bladder component is replaced.

The foregoing is a description of the preferred embodiment of the improved dynamic aortic patch of the present invention. It must be appreciated that many changes and modifications can be made without departing from the spirit of the present invention. The invention, therefore, should be limited only by the following claims.

What is claimed is:

1. In a mechanical auxiliary blood pumping apparatus such as an aortic patch or the like adapted to be surgically implanted in an aortic vessel for assisting blood circulation and including a flexible, air tight bladder to be systematically inflated and deflated by application of fluidic pressure, and an envelope for said bladder having a non-thrombogenic surface facing the interior of the aortic vessel, the improvement comprising: said bladder and said envelope being distinct, separate, independent components of said apparatus, said envelope being adapted to be implanted and sutured into the aortic vessel in a tight, sealing relationship to the intima of the vessel to prevent leakage and loss of blood outwardly of the vessel, with said non-thrombogenic surface facing the interior of said aortic vessel, and said bladder being thereafter removably positioned within said envelope whereby said envelope is permanently implantable without damage to said bladder such as by puncturing during suturing and the like and whereby said bladder is insertable and removable without removal of said envelope and thus without extracorporeal bypass.

2. The invention as defined in claim 1 wherein said flexible bladder is formed of a thin film and has longitudinal filaments therein for preventing the bladder from closing the entrapping fluid therein during deflation of said bladder.

3. The invention as defined in claim 1 wherein said envelope includes a second surface facing the thoracic cavity, said second surface being reinforced by cross-stitching to prevent said second surface from stretching and to thereby direct and limit said bladder inflation inwardly of the aortic vessel.

4. The invention as defined in claim 1 wherein one end of said flexible bladder includes a flexible hollow tube in communication with the interior of the bladder for supplying fluid to said bladder to permit said bladder to be inflated and deflated.

* * * * *